United States Patent
Billeres et al.

(10) Patent No.: US 8,339,128 B2
(45) Date of Patent: Dec. 25, 2012

(54) MAGNETIC-DISTURBER DETECTION METHOD AND DETECTOR, OBJECT-LOCALIZING METHOD AND SYSTEM, RECORDING MEDIUM FOR THESE METHODS

(75) Inventors: Malvina Billeres, Grenoble (FR); Roland Blanpain, Entre-Deux-Guiers (FR)

(73) Assignee: Commissariat a l'energie atomique et aux energies alternatives, Paris (FR)

( * ) Notice: Subject to any disclaimer, the term of this patent is extended or adjusted under 35 U.S.C. 154(b) by 302 days.

(21) Appl. No.: 12/898,011

(22) Filed: Oct. 5, 2010

(65) Prior Publication Data

US 2011/0084692 A1 Apr. 14, 2011

(30) Foreign Application Priority Data

Oct. 14, 2009 (FR) .................................... 09 57205

(51) Int. Cl.
*G01N 27/72* (2006.01)

(52) U.S. Cl. ........................ 324/228; 324/244

(58) Field of Classification Search .................. 324/228, 324/244

See application file for complete search history.

(56) References Cited

U.S. PATENT DOCUMENTS

| | | | |
|---|---|---|---|
| 6,122,538 A * | 9/2000 | Sliwa et al. | 600/407 |
| 6,374,134 B1 * | 4/2002 | Bladen et al. | 600/424 |
| 6,754,609 B2 * | 6/2004 | Lescourret | 702/150 |
| 6,774,624 B2 * | 8/2004 | Anderson et al. | 324/207.17 |

FOREIGN PATENT DOCUMENTS

| | | |
|---|---|---|
| EP | 0 993 804 | 4/2000 |
| EP | 1 502 544 | 2/2005 |

* cited by examiner

*Primary Examiner* — Bot Ledynh
(74) *Attorney, Agent, or Firm* — Occhiuti Rohlicek & Tsao LLP

(57) ABSTRACT

This method for detecting a magnetic disturber method comprises:
- the measurement (52) of the magnetic field emitted by the emitter by at least two triaxial sensors placed at different known positions,
- for each sensor, the determining, (54) from the magnetic field measured by this sensor, of the coordinates of a direction vector collinear with an axis passing through the geometrical center of the emitter and the geometrical center of this sensor, the geometrical center of the emitter being the point at which there is located a magnetic field point source which models this emitter and the sensor being capable of being modeled by a point transducer situated at a point where the magnetic field is measured and constituting the geometrical center of this sensor,
- verification (56; 70) that the smallest distance between the axes, each collinear each with one of the direction vectors, is smaller than a predetermined limit, and
- if this is not the case, the reporting (64) of the presence of a magnetic disturber and, in the contrary situation, not making this report.

11 Claims, 2 Drawing Sheets

MAGNETIC-DISTURBER DETECTION METHOD AND DETECTOR, OBJECT-LOCALIZING METHOD AND SYSTEM, RECORDING MEDIUM FOR THESE METHODS

CROSS-REFERENCE TO RELATED APPLICATIONS

Under 35 USC 119, this application claims the benefit of the Oct. 14, 2009 priority date of French Application No. FR0957205, the contents of which are hereby incorporated by reference in their entirety.

BACKGROUND OF THE INVENTION

The invention pertains to a method for detecting a magnetic disturber (or disturbing element) of the magnetic field emitted by an emitter of an at least triaxial magnetic field. The invention also relates to a method and a system for localizing an object and to a medium for recording information to implement these methods.

A magnetic disturber is defined herein as being any object that degrades or deforms the field lines of a magnetic field emitted in proximity. For example, the disturber may be a conductive part. In this case, the degradation of the magnetic field lines is caused by the appearance of eddy currents in the conductive part. The conductive part may be for example a metal part. The disturber may also be a magnetic part such as a paramagnetic or ferromagnetic part.

A triaxial magnetic field emitter emits a magnetic field along three emission axes that are mutually non-collinear. For example, such an emitter is formed by several aligned uniaxial magnetic field sources, respectively on each of the axes of emission of the emitter.

A uniaxial magnetic field source is a source that preferably emits the magnetic field along only one axis. For example, a coil whose turns are wound about a same axis is a uniaxial magnetic field source and the preferred emission axis coincides with the winding axis of the turns.

Similarly, an at least triaxial emitter is an emitter that emits magnetic fields along more than three non-collinear axes.

A triaxial magnetic field sensor is also defined as a sensor capable of measuring the direction of the magnetic field. Typically, to this effect, these sensors measure the amplitude of the projection of the magnetic field on three mutually non-collinear axes of measurement. Thus, these sensors can be used to measure the direction of the magnetic field and, generally, also the amplitude of this magnetic field.

PRIOR ART

Prior art methods for detecting a magnetic disturber comprise the measurement of the magnetic field emitted by the emitter by at least two triaxial sensors placed at different known positions.

Magnetic-disturber detection methods are used particularly in methods for localizing an object by means of a magnetic system. Indeed, if the measured magnetic field used to localize an object is disturbed, then the localizing of the object will be erroneous. This may have particularly harmful consequences when the localizing method is used in medicine to locate a probe or a catheter within the human body. Indeed, for such applications, it is very important that the localization of the proble should be reliable. Now, in medicine, there are many magnetic disturbers liable to falsify the localization. For example, the magnetic disturber may be an operation table, a surgeon's scalpel, the metal frame of another apparatus placed near the patient, etc.

Several methods have already been proposed to detect disturbers (see for example EP 1 502 544 or EP 0 993 804). These methods use complex computations.

SUMMARY OF THE INVENTION

The invention seeks to remedy this problem by simply detecting the presence of a disturber of the emitted magnetic field.

An object of the invention therefore is a method for detecting a disturber of the emitted magnetic field comprising the following steps:

for each sensor, the determining, from the magnetic field measured by this sensor, of the coordinates of a direction vector collinear with an axis passing through the geometrical center of the emitter and the geometrical center of this sensor, the geometrical center of the emitter being the point at which there is located a magnetic field point source which models this emitter and the sensor being capable of being modeled by a point transducer situated at a point where the magnetic field is measured and constituting the geometrical center of this sensor, verification that the smallest distance between the axes, each collinear with one of the direction vectors, is smaller than a predetermined limit, and if this is not the case, the reporting of, the presence of a magnetic disturber and, in the contrary situation, the absence of such reporting.

The above method is based on the fact that, when there is no disturber and ideally, the axes collinear with the direction vectors must intersect at a point E corresponding to the position of the emitter. The presence of a magnetic disturber modifies the direction of one or more direction vectors. As a consequence, at least one of the axes collinear with these direction vectors no longer intersects the other axes. In this case, the smallest distance d between at least two of these axes is non-zero. This means that, if this distance d exceeds the predetermined limit, then a disturber is present.

This method is simple to implement because the computation of the direction vectors requires only some multiplications and additions. It can therefore be executed very swiftly and can be applied in "real time", even if the sensors and the emitter move rapidly relative to one another. Furthermore, it is particularly sensitive. Indeed, a slight disturbance of the direction of one of the direction vectors can result in a major modification of the minimum distance d.

Finally, it calls for no calibration or practically no calibration whatsoever. Only the positions of the sensors relative to one another must be known beforehand.

The embodiments of this method may include one or more of the following characteristics:

the verifying step is done at least for the first and second direction vectors $\vec{u}_1$ $\vec{u}_2$, and comprises:

the computation of the coordinates of a first vector $\vec{n}_1$ normal to the direction vector $\vec{u}_1$ and to an axis D passing through the geometrical centers of the two sensors used to determine the direction vectors $\vec{u}_1$ and $\vec{u}_2$, the computation of the coordinates of a second vector $\vec{n}_2$ normal to the direction vector $\vec{u}_2$ and the axis D, the computation of the angle between the vectors $\vec{n}_1$ and $\vec{n}_2$, and checking that this angle is below a threshold corresponding to the predetermined limit beyond which the reporting of the magnetic disturber is activated;

the step of verification is at least performed for first and second direction vectors $\vec{u}_1$, $\vec{u}_2$ and comprises:

the computation of the value of a combined product, the combined product being defined by the following relationship: $(\vec{D} \otimes \vec{u}_1) \cdot \vec{u}_2$, where $\otimes$ and '·' are, respectively, the vector and scalar product operations and the vector $\vec{D}$ is a vector collinear with an axis D passing through the geometrical centers of the two sensors used to determine the direction vectors $\vec{u}_1$ and $\vec{u}_2$, and checking that the value of the combined product is below a threshold corresponding to the predetermined limit beyond which the reporting of the magnetic disturber is activated;

the positions of the sensors in a same referential system are fixed.

These embodiments of the detection method furthermore have the following advantages:

computing the angle between the vectors $\vec{n}_1$ and $\vec{n}_2$ increases the precision of detection of the magnetic disturber.

An object of the invention is also a method for localizing an object in a referential system by means of at least one magnetic field emitter that is at least triaxial and at least two magnetic triaxial sensors of this magnetic field emitted by the emitter, each sensor being fixedly linked to the referential system and each emitter being fixedly connected to the object or vice versa, this method comprising:

the emitting of a magnetic field by the emitter and the measuring of this magnetic field by the sensors, the localizing of the object in the referential system from the measurements made by the sensors, the detection of a disturber of the magnetic field emitted by the emitter by using the same sensors as were used at the localizing step and by implementing the above method of detection.

An object of the invention is also an information-recording medium comprising instructions to execute one of the above methods when these instructions are executed by an electronic computer.

An object of the invention is also a detector of a magnetic disturber of a magnetic field emitted by a magnetic field emitter that is at least triaxial, this detector comprising:

at least two triaxial sensors capable of measuring the magnetic field emitted by the emitter, these sensors being places at different known positions, and a processing unit connected to the sensors to process the measurements of the magnetic field of the emitter, this processing unit being capable of:

determining, for each sensor and from the magnetic field measured by this sensor, coordinates of a direction vector collinear with an axis passing through the geometrical center of the emitter and the geometrical center of this sensor, the geometrical center of the emitter being the point at which there is located a magnetic field point source which models this emitter and the sensor being capable of being modeled by a point transducer situated at a point where the magnetic field is measured and constituting the geometrical center of this sensor, verifying that the smallest distance between the axes, each collinear with one of the direction vectors, is smaller than a predetermined limit, and if this is not the case, reporting the presence of a magnetic disturber and, in the contrary situation, not reporting the presence of this magnetic disturber.

Finally, an object of the invention is also a system for localizing an object in a referential system, this system comprising:

at least one magnetic field emitter that is at least triaxial, at least two triaxial sensors to measure the magnetic field emitted by this emitter, the sensors being fixed in the referential system and the emitter or the emitters being fixedly connected to the object or vice versa, the emitting of a magnetic field by the emitter and the measuring of this magnetic field by the sensors, a localizing module capable of localizing the object in the referential system from the measurements made by the sensors, the above detector of a disturber of the magnetic field emitted by the emitter, the sensors of this detector being common with those used by the localizing module.

BRIEF DESCRIPTION OF THE DRAWINGS

The invention will be understood more clearly from the following description, given purely by way of an non-exhaustive example and made with reference to the appended drawings, of which.

In these figures, the same references are used to designate the same elements.

DETAILED DESCRIPTION OF THE INVENTION

Here below in this description, the characteristics and functions well known to those skilled in the art shall not be described in detail.

Figure 1:
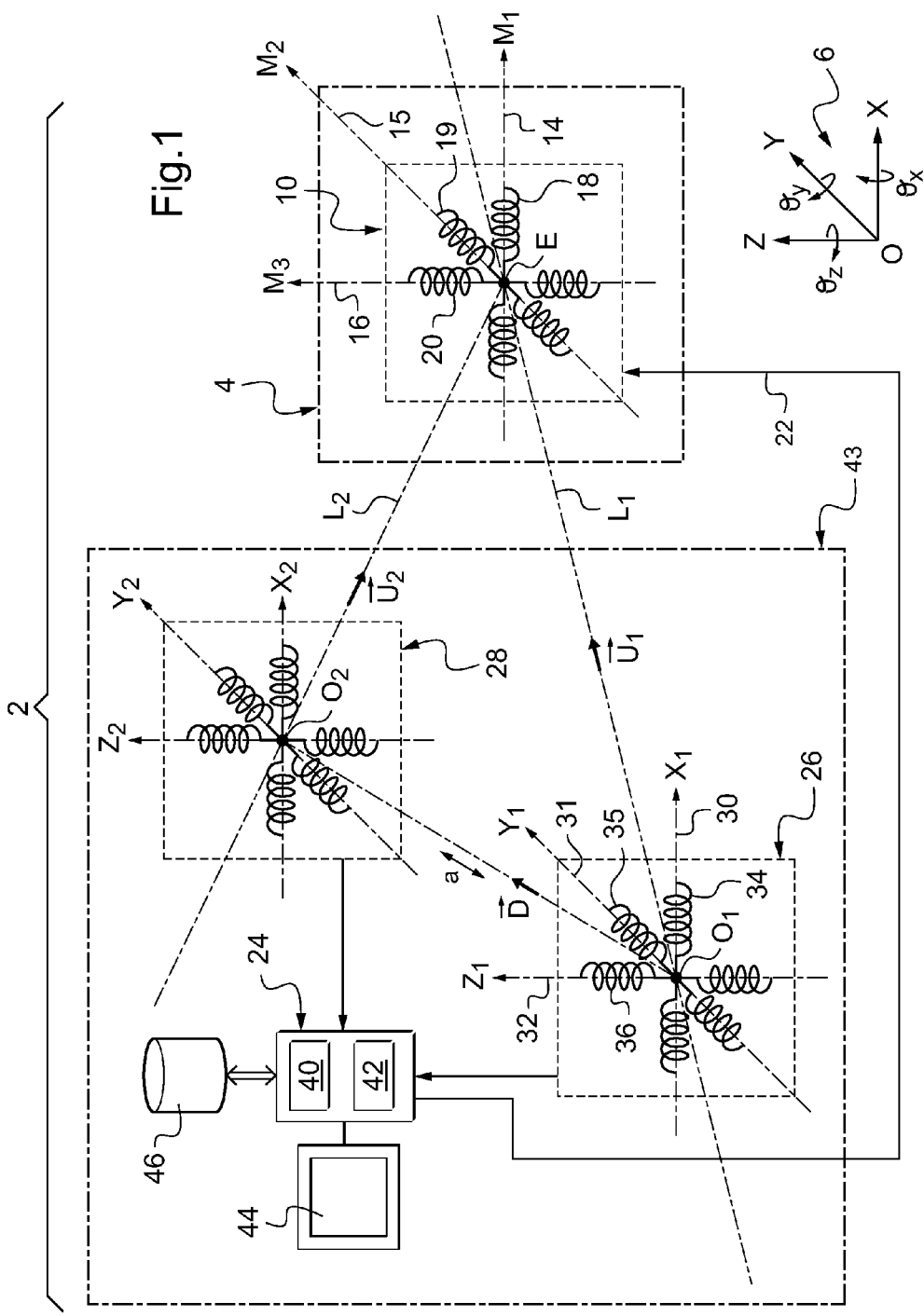
FIG. 1 is a schematic illustration of a system for localizing an object equipped with a magnetic disturber detector.

FIG. 1 represents a system 2 for localizing an object 4 in a referential system 6. For example, the object 4 is a probe or a catheter introduced into the human body. For example, the object 4 is mobile relative to the referential system 6.

The referential system 6 is a fixed referential with three orthogonal axes X, Y, and Z.

The localizing of the object 4 in the referential system 6 consists for example in finding its x, y, z position and its θx, θy, θz orientation. The angles θx, θy and θz represent the orientation of the object 4 respectively about the X, Y and Z axes.

To localize the object 4 in the referential system 6, the object is equipped for example with several magnetic field emitters. To simplify FIG. 1, only one emitter 10 has been shown.

The emitter 10 is a triaxial emitter emitting a magnetic field along three non-collinear axes 14 to 16. Here, these emission axes 14 to 16 are mutually orthogonal. These axes are integral with the object 4. To this end, the emitter 10 incorporates three uniaxial sources 18 to 20 corresponding respectively to the magnetic moments $M_1$, $M_2$ and $M_3$. Each of these sources has only one direction of emission along which the essential part of the magnetic field is emitted. Here, the directions of emission of the sources 18 to 20 respectively coincide with the axes 14 to 16, on which the magnetic moments $M_1$, $M_2$ and $M_3$ are aligned.

Each of these sources 18 to 20 can be modeled by a magnetic field point source. Preferably, the sources 18 to 20 are laid out so that their respective point sources occupy exactly the same position in the referential system 6. This position is identified by a point E. The point E is at the intersection of the axes 14 to 16. The point at which the point sources corresponding to the sources 18 to 20 are superimposed constitutes the geometrical center of the emitter 10. Here, this geometrical center coincides with the barycenter or the center of mass of the sources 18 to 20.

For example, each source 18 to 20 is constituted by a single coil wound respectively about the axes 14 to 16. Here, each of these coils is divided into two identical groups of turns distributed equally on either side of the point E along the winding axis. Each group of turns is coiled in the same sense along the winding axis.

The emitter 10 is powered and controlled by means of a flexible wire link 22 connected to a processing unit 24.

The unit 24 is also connected to several triaxial magnetic field sensors. To simplify FIG. 1, only two sensors 26 and 28 are shown. Each of these sensors is capable of measuring the direction and amplitude of the magnetic field emitted by the emitter 10.

These sensors 26 and 28 are spaced out relatively to each other by a distance a.

The sensor 26 is fixed in the referential system 6. This sensor 26 measures the projection of the magnetic field along three orthogonal axes 30 to 32. Here, these axes 30 to 32 are collinear respectively with the axes $X_1$, $Y_1$ and $Z_1$ of an orthogonal referential system $R_1$ whose center $O_1$ is centered on the sensor 26.

The sensor 26 is herein formed by three uniaxial transducers 34 to 36. Each transducer 34 to 36 measures the projection of the magnetic field emitted respectively on the axes 30 to 32.

For example, each of these transducers 34 to 36 consists of a single coil wound respectively about the axes 30 to 32. As in the case of the emitter 10, each of these coils is divided into two identical groups of turns distributed symmetrically on either side of the point $O_1$ along the winding axis. Each group of turns is wound in the same sense along the winding axis. Thus, each of these transducers 30 to 32 can be modeled by a point transducer where the projection of the magnetic field on the measurement axis is measured. Here, the three point transducers are placed at $O_1$. The point at which the different point transducers are superimposed is the geometrical center of the sensor. Here, this geometrical centre coincides with the barycenter or the center of mass of the transducers.

Such a sensor 26 measures the direction of the magnetic field emitted at the point $O_1$.

The sensor 28 is for example identical to the sensor 26 except that the coils are wound respectively about three axes $X_2$, $Y_2$ and $Z_2$ of an orthogonal referential system $R_2$ whose point of origin $O_2$ coincides with the geometrical center of the sensor 28.

To simplify the computations, the axes $X_2$, $Y_2$ and $Z_2$ are parallel respectively to the axes $X_1$, $Y_1$ and $Z_1$.

Preferably, the distance a is at least two or three times greater than the greatest dimension of one of the sensors. For example, the greatest dimension of the sensor 26 is herein the greatest length of one of the transducers 32 to 34.

The sensors 26 and 28 are also distant from the emitter 10 by a distance at least equal to 2 or 3 times the greatest dimension of the sensor 26 or 28. Thus, the emitter 10 can be modelled like a magnetic field point source centered on the point E.

The unit 24 includes a module 40 for localizing the position of the emitter 10 in the referential system 6 from measurements made by the sensors 26 and 28. For example, the module 40 determines the position and orientation of the object 4 by resolving a system of equations. This system of equations is obtained by modeling the magnetic interactions between the uniaxial sources and the transducers without taking account of the presence of magnetic disturbers. In this system of equations, the position x, y and z and the orientation θx, θy and θz of the object 4 are unknown quantities while the values of the other parameters are obtained from measurements made by the sensors 26 and 28. More information on such systems of equations may be found for example in the patent application EP 1 502 544.

The unit 24 also has a module 42 for detecting the presence of a disturber of the magnetic field emitted by the emitter 10. The working of this module 42 shall be described in detail with reference to FIGS. 2 and 3.

The combining of the sensors 26, 28 and of the module 42 forms a detector 43 of disturbers of the magnetic field emitted by the emitter 10.

The unit 24 is also connected to a man/machine interface 44 used for example to inform the operator that a magnetic disturber has been detected or to indicate the position of the object 4.

The unit 24 is formed by a programmable electronic computer capable of executing these instructions recorded in an information-recording medium. To this end, the unit 24 is connected to a memory 46 comprising the instructions needed to execute the method of FIG. 2 or 3.

The working of the system 2 shall now be described in greater detail with respect to the method of FIG. 2.

At a step 50, the emitter 10 emits a magnetic field, for example sequentially along each of the axes 14 to 16.

At the same time, at a step 52, each of the sensors 26 and 27 measures the magnetic field emitted by the emitter 10.

Then, at a step 54, the detection module 42 determines direction vectors $\vec{u}_1$ and $\vec{u}_2$, directed respectively from the point $O_1$ to the point E or vice versa and from the point $O_2$ to the point E or vice versa. In FIG. 1, these vectors are represented as being both directed towards the point E.

In the above-described operative conditions, the emitter 10 emits a field approximated to a dipolar field. Thus, the magnetic field emitted by an uniaxial source and measured by the triaxial sensor 26 is given by the following relationship:

$$H_i = 100 \cdot \frac{3 * u_1 * u_1^T - I}{R^3} M_i$$

where:
the index i is the identifier of one of the uniaxial sources 18 to 20,
$M_i$ is the column matrix associated with the magnetic moment of the uniaxial source i of the emitter 10,
"I" is the identity matrix,
$u_1$ is a column matrix containing the coordinates of the direction vector $\vec{u}_1$ expressed in the referential system $R_1$,
R is the distance between the emitter 10 and the sensor 26, and $H_i$ is the column matrix containing the coordinates of the magnetic field measured along the three axes 30 to 32 of the sensor 26, the symbol "$^T$" represents the transposed operation.

Here below in this description, $H_1$, $H_2$ and $H_3$ denote the column matrices containing the measurements along the axes 30 to 32 of the magnetic field emitted respectively by the uniaxial sources 18, 19 and 20. With these notations, the coordinates of the vector $\vec{u}_1$ in the referential system $R_1$ are obtained using the following relationship:

$$\vec{u}_1 = [H_1*(H_2^T*H_3) - H_3*(H_1^T*H_2)] \otimes [H_2*(H_3^T*H_1) - H_3*(H_1^T*H_2)]$$

Similarly, at the step 54, the module 52 also determines the coordinates of a direction vector $\vec{u}_2$ pointing from the point $O_2$ to the point E.

Here, the terms $L_1$ and $L_2$ denote the axes collinear with the direction vectors $\vec{u}_1$ and $\vec{u}_2$.

Since the sensors 26 and 28 measure the magnetic field emitted by the same emitter when there is no disturbance, the axes $L_1$ and $L_2$ must intersect at the point E. However, in practice, because of noise in the measurement and computation error, the axes $L_1$ and $L_2$ do not intersect, but pass proximately to each other at the point E. Thus, the smallest distance d between the axes $L_1$ and $L_2$ is small. Conversely, if a magnetic disturber is present, it appreciably modifies the direction of the vector $\vec{u}_1$ or $\vec{u}_2$ so that the smallest distance d becomes great.

Thus, at a step 56, it is ascertained that the distance d between the axes $L_1$ and $L_2$ is below a predetermined limit.

For example, to this end, in an operation 58, the module 42 computes the coordinates in the referential system $R_1$ of a vector $\vec{n}_1$ normal to the vector $\vec{u}_1$ and to a vector $\vec{D}$. The vector $\vec{D}$ is a vector collinear with an axis D passing through the points $O_1$ and $O_2$. The coordinates of this vector $\vec{D}$ in the referential system $R_1$ can easily be determined from the coordinates of the points $O_1$ and $O_2$ in the referential system 6 since the position of the sensors 26 and 28 is herein fixed.

For example, the coordinates of the vector $\vec{n}_1$ are computed by means of the following relationship:

$$\vec{n}_1 = \vec{D} \otimes \vec{u}_1$$

where:

$\otimes$ is the vector product operation.

Similarly, at the operation 58, the coordinates of a vector $\vec{n}_2$ normal to the vector $\vec{u}_2$ and to the vector $\vec{D}$ are computed. The coordinates of the vector $\vec{n}_2$ are for example expressed in the referential system $R_1$.

Then, in an operation 60, the angle $\theta$ between the vectors $\vec{n}_1$ and $\vec{n}_2$ is computed. Given that here the axes of the referential systems $R_1$ and $R_2$ are parallel, this angle $\theta$ can be computed directly by means of the following relationship:

$$\theta = \mathrm{acos}\left(\frac{\vec{n}_1 \cdot \vec{n}_2}{\|\vec{n}_1\| * \|\vec{n}_2\|}\right)$$

where:

"a cos" represents the arc cosine operation, the symbol "·" represents the scalar product, the symbol "*" represents the multiplication between two values, "$\|\ldots\|$" represents the Euclidian norm of a vector.

Depending on the directions of the vectors $\vec{u}_1$ and $\vec{u}_2$, this angle $\theta$ must be close to 0° or close to 180° when there is no magnetic disturber. It is assumed here that the directions of the vectors $\vec{u}_1$ and $\vec{u}_2$ are such that the angle $\theta$ must be close to 0° when there is no magnetic disturber.

Then, in the operation 62, the angle $\theta$ is compared with a threshold $S_1$ to ascertain that the distance d is below a predetermined limit.

If this threshold $S_1$ is crossed, then it means that a magnetic disturber is present. Then, a step 64 is performed, in which the presence of this magnetic disturber is reported. For example, this presence is reported by means of the man/machine interface 44. The reporting can thus consist simply of an operation for taking account of this piece of information in the processing operations performed by the unit 24 without necessarily informing the user of it.

If not, if the angle $\theta$ is below the threshold $S_1$, then it means that there is no magnetic disturber. The operation then goes to a step 66 during which, for example, the module 40 determines the localization of the emitter 10 in the referential system 6 from the measurements made by the sensors 26 and 28.

At the end of the steps 50, 64 and 66, the method returns to the steps 50 and 52.

Figure 2:
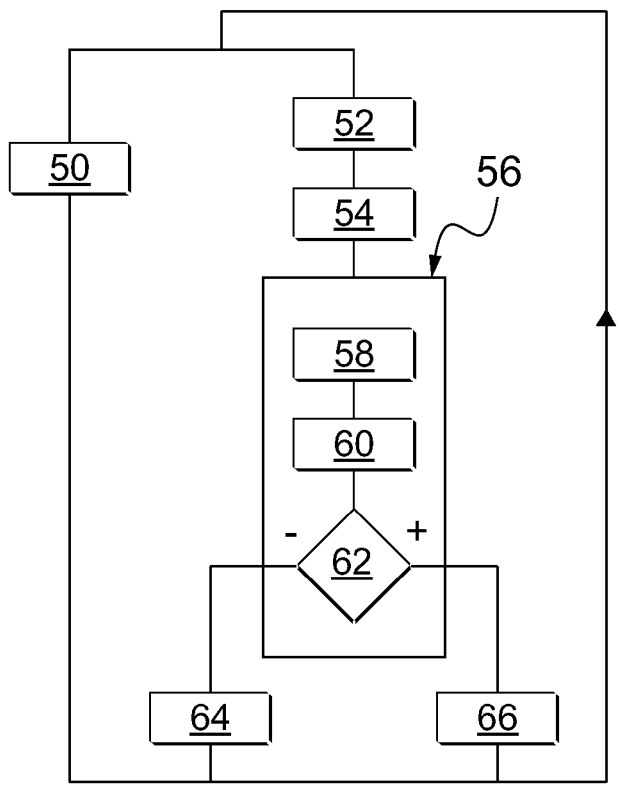
FIG. 2 is a flowchart of a method for detecting a magnetic disturber and for localizing an object by means of the system of FIG. 1.
Figure 3:
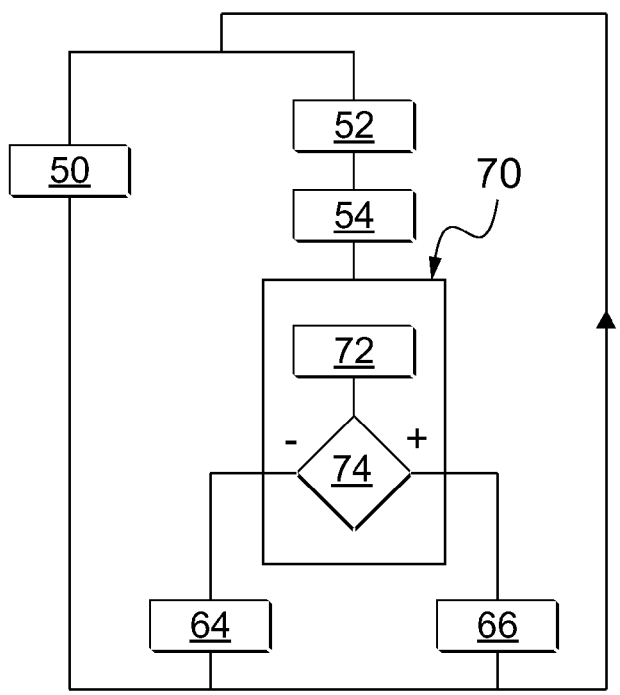
FIG. 3 is a flowchart of another embodiment of a method for detecting a magnetic disturber and for localizing an object by means of the system of FIG. 1.

The method of FIG. 3 is identical to the method of FIG. 2 except that the step 56 is replaced by a step 70. At the beginning of this step 70, during an operation 72, the combined product P between the vectors $\vec{u}_1$ and $\vec{u}_2$ is computed according to the following relationship:

$$P = (\vec{D} \otimes \vec{u}_1) \cdot \vec{u}_2$$

where:

P is the combined product of the vectors $\vec{u}_1$ and $\vec{u}_2$.

Then, the operation passes to a step 74 for comparing the value of the combined product P with a threshold $S_2$ to ascertain the distance d is below a predetermined limit. When there is no disturber, the value of the combined product must be close to zero. Conversely, the presence of a disturber results in a high value of this combined product P.

Thus, if the value of the combined product P is below the predetermined threshold $S_2$, then the operation goes to the step 66. If not, it goes to the step 64.

Many other embodiments are possible. For example, the emitter can have more than three axes of emission. In this case, the magnetic field emissions on the supplementary axes beyond three are such that there is redundancy in the information measured by the sensors. This redundancy can be used thereafter to overcome the disturbances caused by the magnetic disturber in applications such as the localization of the position of the object 4 relatively to the sensor.

This emitter 10 can emit the magnetic field on each of its axes sequentially in time or at the same time. In the latter case, preferably, the fields will be emitted at different frequencies on each of the axes so that they can be distinguished from one another on the sensor side.

Methods other than those given here above can be used to compute the coordinates of the direction vectors. In particular, the direction vectors could originate in the geometrical centre of the emitter and point towards the respective sensors.

The axes of the referential systems $R_1$ and $R_2$ are not necessarily parallel. In this case, a change of referential system is made on the coordinates of one of the direction vectors $\vec{u}_1$ or $\vec{u}_2$ so that the coordinates of these two vectors are expressed in the same referential system before the vectors $\vec{n}_1$ and $\vec{n}_2$ or the combined product P are computed.

The magnetic disturber detector can have more than two triaxial sensors.

The verification that the smallest distance d between the axes $L_1$ and $L_2$ is smaller than a predetermined limit can be obtained by methods other than those described here above. For example, it is possible to determine the equation of these axes in a same referential system and then compute the smallest distance d between these two axes on the basis of these equations before comparing this distance with the predetermined limit.

Here, the system 2 has been described in the particular case where the emitter is mobile and the sensors are fixed. However, the description here applies to the reverse case in which the emitter is fixed and the sensors are mobile in the referential system 6.

It is not necessary for the sensors to be fixed in the referential system 6. On the contrary, what is necessary is that the relative position of the emitter with respect to the sensors should not vary between the point in time when one of the sensors performs its measurements and the point in time when the other sensor performs its measurements. For example, this condition is also met provided that the measurements of the sensors are made at the same time, even if the sensors move in the referential system.

If the position of the sensors is not fixed, the relative position of a sensor with respect to the other one must be known before one of the above-described methods is executed. The term "known" position means that at least the direction or the norm of the vector $\vec{D}$ is known and, preferably, that its direction is known or that its direction and its norm are also known. There are many possible methods of knowing the relative position of sensor with respect to the other. For example, a Kalman filter can be used to this effect. More specifically, this Kalman filter is built on the basis of the equations of electromagnetism linking the magnetic fields emitted to the magnetic fields measured. In these equations, the unknowns are the positions of the sensors and possibly the position of the emitter.

In one variant, only the direction of the vector $\vec{D}$ is known and its norm is unknown. In this variant, the norm of the vector $\vec{D}$ is chosen to be equal to an arbitrary value, for example equal to one. Then, a learning phase is implemented to adjust the valuation of the threshold $S_1$ or $S_2$ beyond which the presence of a disturber is detected. For example, this variant is identical to the method of FIG. 2 except that only the direction of the vector $\vec{D}$ is known. The value of the thresholds $S_1$ or $S_2$ can be independent of the norm of the vector $\vec{D}$, for example, if all the vectors used are normalized.

To simplify the sensors 26 and 28, they can be formed by a single turn each.

The methods and the system described here above can be used in many different fields of application other than the medical field. For example, the system can be used to localize a vacuum cleaner in a room or to localize a person such as a child carrying a magnetic emitter.

The invention claimed is:

1. A method for detecting a magnetic disturber of an at least triaxial emitter of a magnetic field, the method comprising:
   measuring the magnetic field emitted by the emitter using at least two triaxial sensors placed at different known positions,
   for each sensor, determining, from the magnetic field measured by the sensor, the coordinates of a direction vector collinear with an axis passing through the geometrical center of the emitter and the geometrical center of the sensor, the geometrical center of the emitter being the point at which there is located a magnetic field point source that models the emitter, and wherein the sensor is capable of being modeled by a point transducer situated at a point where the magnetic field is measured and constituting the geometrical center of the sensor,
   determining whether the smallest distance between the axes, each of which is collinear with one of the direction vectors, is smaller than a predetermined limit, and
   if the smallest distance is not smaller than the predetermined limit, reporting the presence of a magnetic disturber.

2. The method according to claim 1, wherein verifying is done at least for first and second direction vectors, and wherein verifying comprises:
   computing coordinates of a first vector normal to the direction vector and to an axis passing through the geometrical centers of the two sensors used to determine the direction vectors,
   computing the coordinates of a second vector normal to the direction vector and the axis,
   computing the angle between the first and second vectors, and
   checking that the angle is below a threshold corresponding to the predetermined limit beyond which the reporting of the magnetic disturber is activated.

3. The method according to claim 1, wherein verifying is at least performed for first and second direction vectors $u_1$ and $u_2$, and wherein verifying comprises
   computing the value of a combined product, the combined product being defined by $(D \otimes u_1) \cdot u_2$ where "$\otimes$" is a vector product operator and "·" is a scalar product operator, and wherein the vector D is a vector collinear with an axis D passing through the geometrical centers of the two sensors used to determine the direction vectors $u_1$ and $u_2$, and
   checking that the value of the combined product is below a threshold corresponding to the predetermined limit beyond which the reporting of the magnetic disturber is activated.

4. The method according to claim 1, wherein the positions of the sensors in a same referential system are fixed.

5. A method for localizing an object in a referential system using at least one magnetic field emitter that is at least triaxial and at least two triaxial sensors of the magnetic field emitted by the emitter, each sensor being fixed in the referential system and each emitter being fixedly related to the object or vice versa, the method comprising:
   causing the emitter to emit a magnetic field by the emitter and causing the sensors to measure the emitted magnetic field,
   localizing the object in the referential system from the measurements made by the sensors,
   detecting a disturber of the magnetic field emitted by the emitter by using the same sensors as were used for localizing the object and by implementing a method according to claim 1.

6. The method of claim 1, further comprising,
   if the smallest distance is smaller than the predetermined limit, declining to report the presence of a magnetic disturber.

7. A non-transitory computer-readable medium having encoded thereon software for detecting a magnetic disturber of an at least triaxial emitter of a magnetic field, said software comprising instructions that, when executed by a digital computer, cause the computer to execute the method recited in claim 1.

8. A detector of a magnetic disturber of a magnetic field emitted by a magnetic field emitter that is at least triaxial, the detector comprising:
- at least two triaxial sensors capable of measuring the magnetic field emitted by the emitter, the sensors being placed at different known positions, and
- a processing unit connected to the sensors to process the measurements of the magnetic field of the emitter, the processing unit being configured for
  - determining, for each sensor and from the magnetic field measured by the sensor, coordinates of a direction vector collinear with an axis passing through the geometrical center of the emitter and the geometrical center of the sensor, the geometrical center of the emitter being the point at which there is located a magnetic field point source that models the emitter and the sensor being capable of being modeled by a point transducer situated at a point where the magnetic field is measured and constituting the geometrical center of the sensor,
  - determining whether the smallest distance between the axes, each of which is collinear with one of the direction vectors, is smaller than a predetermined limit, and
  - if the smallest distance is not smaller than the predetermined limit, reporting the presence of a magnetic disturber.

9. The detector according to claim 8, wherein the positions of the sensors in a same referential system are fixed.

10. The detector of claim 8, wherein the processing unit is further configured for declining to report the presence of the magnetic disturber if the smallest distance is smaller than the predetermined limit.

11. A system for localizing an object in a referential system, the system comprising:
- at least one magnetic field emitter, the magnetic field emitter being at least a triaxial magnetic field emitter,
- at least two triaxial sensors to measure a magnetic field emitted by the emitter, the sensors being fixed in the referential system and the emitter or the emitters being fixedly connected to the object, or vice versa,
- a localizing module capable of localizing the object in the referential system from the measurements made by the sensors, and
- a detector as recited in claim 8, the sensors of the detector being the same as the sensors used by the localizing module.

* * * * *